(12) United States Patent
Maeda et al.

(10) Patent No.: US 8,377,180 B2
(45) Date of Patent: Feb. 19, 2013

(54) OXYGEN CONCENTRATOR (75) Inventors: Akihiro Maeda, Chiyoda-ku (JP); Makoto Ando, Hino (JP)

(73) Assignee: Teijin Pharma Limited, Tokyo (JP)

( * ) Notice: Subject to any disclaimer, the term of this patent is extended or adjusted under 35 U.S.C. 154(b) by 306 days.

(21) Appl. No.: 12/741,909

(22) PCT Filed: Nov. 13, 2008

(86) PCT No.: PCT/JP2008/070670
§ 371 (c)(1),
(2), (4) Date: May 7, 2010

(87) PCT Pub. No.: WO2009/063938
PCT Pub. Date: May 22, 2009

(65) Prior Publication Data
US 2010/0242734 A1  Sep. 30, 2010

(30) Foreign Application Priority Data

Nov. 15, 2007 (JP) .............................. 2007-296494
Mar. 27, 2008 (JP) .............................. 2008-083349

(51) Int. Cl.
*B01D 53/047* (2006.01)
*A61M 16/10* (2006.01)
(52) U.S. Cl. ............................. 96/110; 96/111; 96/112
(58) Field of Classification Search ............ 96/109–112, 96/115, 116, 121; 95/1, 8, 12, 14, 23, 130; 128/204.21, 205.12, 205.27
See application file for complete search history.

(56) References Cited

U.S. PATENT DOCUMENTS

| | | | |
|---|---|---|---|
| 4,323,370 A | 4/1982 | Leitgeb | |
| 4,472,177 A | 9/1984 | Sircar | |
| 5,247,826 A | 9/1993 | Frola et al. | |
| 5,746,806 A | 5/1998 | Aylsworth et al. | |
| 6,960,246 B2 * | 11/2005 | Fujimoto | 96/110 |
| 7,682,428 B2 * | 3/2010 | Nawata et al. | 96/113 |

FOREIGN PATENT DOCUMENTS

| | | |
|---|---|---|
| EP | 0 760 247 A2 | 3/1997 |
| EP | 1 661 596 A2 | 5/2006 |
| JP | 09-311119 A | 12/1997 |

(Continued)

OTHER PUBLICATIONS

Machine generated English translation of JP 2007-000340 A, published Jan. 2007.*

(Continued)

*Primary Examiner* — Frank Lawrence, Jr.
(74) *Attorney, Agent, or Firm* — Sughrue Mion, PLLC (57) ABSTRACT

The present invention provides an apparatus which stably provides highly concentrated oxygen to a patient, regardless of an environmental temperature and/or a highly concentrated oxygen gas flow rate. The present invention is an oxygen concentrator characterized in that an oxygen concentration sensor detecting a concentration of the oxygen gas produced by the oxygen concentrator, a temperature sensor measuring an environmental temperature and/or a flow rate sensor are provided, a control increasing/decreasing a supply airflow volume of the compressed air supply device based on a detected oxygen concentration detected value to maintain an oxygen concentration at a predetermined concentration is performed, and a control device is switched based on a value measured by the temperature sensor and/or flow rate sensor of the apparatus.

12 Claims, 3 Drawing Sheets
(1 of 3 Drawing Sheet(s) Filed in Color)

FOREIGN PATENT DOCUMENTS

| | | |
|---|---|---|
| JP | 11-347127 A | 12/1999 |
| JP | 2002-253675 A | 9/2002 |
| JP | 2005-312982 A | 11/2005 |
| JP | 2006-141896 A | 6/2006 |
| JP | 2007-000340 A | 1/2007 |

OTHER PUBLICATIONS

Machine generated English translation of JP 2006-141896 A, published Jun. 2006.*

European Search Report issued in corresponding Application No. 08848798, dated Nov. 10, 2011.
Chinese Office Action issued on Jan. 4, 2012 in Chinese Application No. 200880116037.3.
Office Action issued by Singapore Patent Office for Application No. 201002771-2 dated Jan. 27, 2011.
Japanese Office Action issued in Japanese Patent Application No. 2009-541164 dated Apr. 3, 2012.
Extended European Search Report issued in European Application No. 12171628.6 dated Aug. 21, 2012.

* cited by examiner

Solid line: a supply airflow volume on start-up
Dotted line: a supply airflow volume that can secure an oxygen concentration at a predetermined concentration at less than 5°C

| Region | Supply airflow volume increased | Supply airflow volume decreased |
|--------|---------------------------------|---------------------------------|
| A      | Good                            | Good                            |
| B      | Good                            | Poor                            |

Figure 3

OXYGEN CONCENTRATOR

TECHNICAL FIELD

The present invention relates to an oxygen concentrator which selectively eliminates nitrogen gas from raw material air using an adsorbent selectively adsorbing nitrogen gas molecules relative to oxygen gas molecules to produce oxygen-enriched air and supply it to users.

BACKGROUND ART

In recent years, the number of patients suffering from respiratory diseases such as asthma, pulmonary emphysema, chronic bronchitis and the like has tended to increase. One of the most effective therapeutic methods for these diseases is oxygen inhalation therapy and oxygen concentrators which separate oxygen-concentrated gas directly from an oxygen tank or air have been developed and used as therapeutic apparatus for oxygen inhalation therapy.

As the oxygen concentrator, a pressure swing adsorption-type (hereinbelow refer to as PSA-type) oxygen concentrator, which produces a highly concentrated oxygen gas by introducing compressed air from a compressor into an adsorption cylinder filled with an adsorbent such as zeolites and the like selectively adsorbing a nitrogen gas to eliminate selectively a nitrogen gas in the air, has widely been used.

The PSA-type oxygen concentrator produces a highly concentrated oxygen gas from air through the steps described below. Firstly, compressed air is supplied by a compressor into an adsorption cylinder to adsorb a nitrogen gas contained in air by an adsorbent such as zeolites and the like. The oxygen concentration in air is increased by selective adsorption and elimination of a nitrogen gas. The highly concentrated oxygen gas thus obtained is transferred to a buffer (product tank) storing oxygen gas via a check valve which is installed to prevent the gas from flowing back and is stored therein.

At the same time, a nitrogen gas adsorbed by the adsorbent is desorbed from the adsorbent by reducing the inner pressure of the adsorption cylinder to recover the efficiency of the adsorbent. A small amount of concentrated oxygen gas may also be supplied into the adsorption cylinder to promote the desorption of nitrogen.

Thus, highly concentrated oxygen-enriched air having an oxygen concentration as high as 95% may be obtained from air by repeatedly pressurizing and depressurizing the adsorption cylinder using the PSA-type oxygen concentrator. In recent years, as such a PSA-type oxygen concentrator, a multiple cylinder-type oxygen concentrator has been used, which is equipped with multiple adsorption cylinders filled with an adsorbent selectively adsorbing a nitrogen gas and in which oxygen concentration efficiency is increased by successively switching these adsorption cylinders by a rotary valve.

It has been known that an oxygen concentration obtained largely depends on the pressure of air to be compressed by a compressor in the PSA-type oxygen concentrator. It is thus required, in order to obtain a highly concentrated oxygen gas, to increase the capacity of the compressor to meet an increase in the pressure of air to be supplied to the adsorption cylinder as far as possible. A problem arises, however, that power consumption of apparatus increases with the elevation of the capacity of the compressor to supply compressed air.

Various attempts had been made as measures for solving these problems of the PSA-type oxygen concentrator. Patent Document 2 discloses a PSA-type oxygen concentrator which realizes reduction in electric power consumption of the apparatus by changing the supply capacity of a compressed air supply device such as a compressor and the like based on a value detected by an oxygen concentration detector for oxygen gas to control oxygen concentrations at a constant value.

Patent Document 1: Japanese Patent Laid-open Publication No. 2006-141896

Patent Document 2: Japanese Patent Laid-open Publication No. 2007-000340

Patent Document 3: Japanese Patent Laid-open Publication No. 2002-253675

DISCLOSURE OF THE INVENTION

Problems to be Solved by the Invention

With the PSA-type oxygen concentrator utilizing an adsorbent, when a raw material air supply volume from a compressed air supply device such as a compressor and the like and an adsorption process sequence are constant, an oxygen concentration of a concentrated oxygen gas thus obtained generally changes depending on environmental (supplied air) temperature. When the temperature is high due to properties of an adsorbent, the amount of the nitrogen adsorbed by the adsorbent decreases, and thus nitrogen breaks through to decrease the oxygen concentration of a product. When the temperature is low, although the amount of nitrogen adsorbed by the adsorbent increases, the oxygen concentration of a product decreases due to insufficient nitrogen desorption caused by a decrease in adsorption speed.

In recent years, as shown in Patent Document 1, a method has been proposed, in which highly concentrated oxygen is secured by changing the capacity of a compressed air supply device such as a compressor and the like based on surrounding environment temperature. Since the pressure of air to be introduced into the adsorption cylinder is required as high as possible and the capacity of the compressed air supply device such as a compressor and the like is required to be elevated in such an apparatus, however, problems such as increased electric power consumption of the apparatus arise.

Patent Document 2 describes a PSA-type oxygen concentrator which realizes low electric power consumption by changing supply capacity of a compressed air supply device such as a compressor and the like based on a value detected by a device detecting oxygen concentration of an oxygen gas. In the PSA-type oxygen concentrator utilizing an adsorbent, however, adsorption property differs depending on environmental temperature and response time to oxygen concentration/supply capacity when the supply capacity of the compressed air supply device such as a compressor and the like is charged differs depending on environmental temperature. Accordingly, a control device must be changed.

Especially in low-temperature environment as compared with high temperatures, since it takes a longer time to stabilize the process, response of oxygen concentration is slower and it takes a longer time until a decrease in product concentration appears. When such an apparatus is operated in low-temperature environment, a stabilization time of oxygen concentration against the operation of a compressed air supply device such as a compressor and the like, namely, a response time of oxygen concentration is extremely slow, and a high oxygen concentration condition may continue while the absorption process remains unstable. Accordingly, the capacity of a compressed air supply device such as a compressor and the like is reduced, in response to a detected oxygen concentration, to a level lower than that for a raw material air volume essentially required. When the process is stabilized later, since the capacity of the raw material air supply device has been decreased to the level lower than that for the amount of air essentially required, an oxygen concentration may rapidly drop to deteriorate QOL of a user.

In addition, as shown in Patent Document 3, an apparatus is proposed, which comprises an oxygen concentration detection device and controls an oxygen concentration of a produced product gas at constant by changing the capacity of a compressed air supply device such as a compressor and the like in response to a detected oxygen concentration. Such an apparatus intends to reduce the electric power consumption by reducing the capacity of the raw material air supply device when the device is new and has high oxygen concentration capacity.

With the oxygen concentrator in general, when a volume of raw material air supplied from a compressed air supply device such as a compressor and the like is constant, oxygen concentration of the obtained concentrated oxygen gas is changed depending on a flow rate for isolating the product. In other words, when a flow rate for isolating the product gas is high, an oxygen concentration of the product gas decreases; when a flow rate for isolating the product gas is low, an oxygen concentration of the product gas increases.

Since a patient using an oxygen concentrator inhales oxygen through a nasal cannula via an extension tube connected to the apparatus, the nasal cannula and extension tube which are oxygen supply devices are flattened by the patient body during sleeping and the like so that the patient cannot sometimes inhale the oxygen at an oxygen flow rate essentially to be inhaled.

In the apparatus described in Patent Document 3, when a product flow rate decreases due to flattening of a tube and the like, an oxygen concentration transiently increases and thus control is performed to decrease the capacity of the compressed air supply device such as a compressor and the like. When the tube recovers from flattening and the product flow rate returns to normal under this condition, the capacity of the compressed air supply device such as a compressor becomes insufficient, on the contrary, to decrease the oxygen concentration and thus oxygen concentration abnormality alarm which is essentially unnecessary may be activated.

In addition, when a flow rate sensor which detects an oxygen flow rate is provided in apparatus such as that described in Patent Document 3 and an oxygen flow rate is adjusted using a flow rate adjustment device such as a proportional valve and the like based on a value detected by the flow rate sensor, an oxygen supply volume may be higher than the oxygen flow rate to be essentially inhaled by a patient, if the flow rate sensor cannot detect a flow rate exactly or the flow rate adjustment device cannot adjust a flow rate exactly. Since an oxygen concentration decreases when an oxygen flow rate to be isolated increases, control is performed to increase the capacity of a compressed air supply device such as a compressor and the like in order to compensate the reduction. When a product flow rate returns to normal, electric power consumption may increase unduly to increase economic burden to a patient.

Means to Solve the Problems

The present invention is to provide an oxygen concentrator which attempts to reduce electric power consumption by decreasing the capacity of a raw material air supply device, which provides highly concentrated oxygen to a patient by low electric power consumption stably regardless of increase/decrease in environmental temperature and/or a certain amount of oxygen flow rate.

In addition, the present inventors have found that, by providing, in addition to controlling the supply capacity of a raw material air supply device based on a detected oxygen concentration value, an oxygen flow rate detection sensor to perform control which does not allow changes in supply capacity of the raw material air supply device when a detected flow rate value is outside a predetermined set value, the raw material air volume does not change even when an oxygen flow rate is decreased by, for example, tube flattening so that an oxygen concentration may be maintained even when a product flow rate returns to normal.

Further, the inventors have found that, by performing control similar to that described above, for example, even when a flow rate sensor cannot detect exactly or a flow rate adjustment device cannot adjust a flow rate exactly and an oxygen flow rate becomes larger than the oxygen flow rate essentially to be inhaled by a patient, a raw material air volume does not change, and thus when a product flow rate returns to normal, increased electric power consumption due to setting of the capacity of a compressed air supply device duly high is prevented.

In an oxygen concentrator having such a control device, a predetermined threshold of a value detected by the flow rate sensor can be allocated individually in accordance with a set value of a flow rate setting device of an oxygen concentrator or independently of a set flow rate.

Since a flow rate sensor generally mounted on an oxygen concentrator for medical use is required to have accuracy of about ±10% of a set flow rate as described in the International Standard ISO8359 and Japanese Industrial Standard JIST7209, however, it is desirable that a predetermined threshold of a value detected by a flow rate sensor be set at a set flow rate ±10% and that the capacity of the compressed air supply device is not allowed to change when a detected flow rate is +10% or higher or −10% or lower.

In addition, as the oxygen concentration sensor used in the oxygen concentrator, a zirconia-type sensor and an ultrasonic-type sensor are generally used, and as the flow rate sensor, an ultrasonic-type sensor and a heat wire-type sensor are generally used.

In other words, the present invention is as follows.
(1) An pressure swing adsorption-type oxygen concentrator provided with an adsorption bed filled with an adsorbent selectively adsorbing nitrogen relative to oxygen and a compressed air supply device supplying compressed air to the adsorption bed, adsorbing and eliminating nitrogen in raw material air to produce unadsorbed oxygen and supplying an oxygen gas at a predetermined flow rate by a flow rate setting device, wherein
the oxygen concentrator is composed of
an oxygen concentration sensor detecting a concentration of an oxygen gas produced by the oxygen concentrator, and
a temperature sensor measuring an environmental temperature;
the oxygen concentrator is a pressure swing adsorption-type oxygen concentrator characterized by performing a control which increases/decreases a supply airflow volume of the compressed air supply device based on a detected oxygen concentration value to maintain an oxygen concentration at a predetermined concentration, and being equipped with a temperature dependent control device controlling a supply airflow volume of the compressed air supply device based on a value detected by the temperature sensor when the value detected by the temperature sensor is outside a predetermined threshold.
(2) The oxygen concentrator described in (1), wherein the temperature dependent control device is a control device performing a control without allowing the supply airflow volume of the compressed air supply device to decrease when the temperature sensor detects a value lower than a predetermined lower temperature limit of the threshold during running of the oxygen concentrator.

(3) The oxygen concentrator described in (1), wherein the temperature dependent control device is a control device performing a control without allowing the supply airflow volume of the compressed air supply device to decrease when the temperature sensor detects a value lower than a predetermined lower temperature limit of the threshold and the supply airflow volume is lower than a predetermined airflow volume during running of the oxygen concentrator.

(4) The oxygen concentrator described in any of (1) to (3), wherein the temperature dependent control device is a device performing a control that makes a supply airflow volume of the compressed air supply device to be higher than a supply airflow volume corresponding to an oxygen concentration value detected by the oxygen concentration sensor, regardless of the value detected by the oxygen concentration sensor when the temperature sensor detects a value lower than a predetermined lower temperature limit of the threshold on start-up of the oxygen concentrator.

(5) The oxygen concentrator described in any of (2) to (4), wherein the lower temperature limit is 5° C.

(6) An oxygen concentrator provided with an adsorption bed filled with an adsorbent selectively adsorbing nitrogen relative to oxygen and a compressed air supply device supplying compressed air to the adsorption bed and adsorbing and eliminating nitrogen in raw material air to produce unadsorbed oxygen and supplying an oxygen gas at a predetermined flow rate by a flow rate setting device, wherein the oxygen concentrator is composed of an oxygen concentration sensor detecting a concentration of an oxygen gas produced, and a flow rate sensor measuring an oxygen gas flow rate, the oxygen concentrator performing a control increasing/decreasing a supply airflow volume of the compressed air supply device based on a detected oxygen concentration value to maintain an oxygen concentration at a predetermined concentration, and a flow rate dependent control device performing a control without allowing the supply airflow volume of the compressed air supply device to change when the value detected by the flow rate sensor is outside the predetermined range.

(7) The oxygen concentrator described in (6), wherein a threshold of a value detected by the flow rate sensor is allocated individually in accordance with a set value of the flow rate setting device or independently of a set flow rate value.

(8) The oxygen concentrator described in (7), wherein a flow rate dependent control device is a device performing a control without allowing the supply airflow volume of the compressed air supply device to change, regardless of a value detected by the oxygen concentration sensor when the value detected by the flow rate sensor is +10% or higher or −10% or less of a set value of the flow rate setting device.

(9) The oxygen concentrator described in any of (6) to (8), wherein the flow rate sensor is an ultrasonic-type flow rate sensor or a heat wire-type flow rate sensor.

(10) An oxygen concentrator provided with an adsorption bed filled with an adsorbent selectively adsorbing nitrogen relative to oxygen, and a compressed air supply device supplying compressed air to the adsorption bed, adsorbing and eliminating nitrogen in raw material air to produce unadsorbed oxygen and supplying an oxygen gas at a predetermined flow rate by a flow rate setting device, wherein the oxygen concentrator is composed of an oxygen concentration sensor detecting a concentration of an oxygen gas produced by the oxygen concentrator, a temperature sensor measuring an environmental temperature, and a flow rate sensor measuring an oxygen gas flow rate, performing a control which increasing/decreasing a supply airflow volume of the compressed air supply device based on a detected oxygen concentration value to maintain an oxygen concentration at a predetermined concentration, a temperature dependent control performing a control a supply airflow volume of the compressed air supply device based on a value detected by the temperature sensor when the value detected by the temperature sensor is outside a predetermined threshold, and a control device performing a flow rate dependent control without allowing the supply airflow volume of the compressed air supply device to change when the value detected by the flow rate sensor is outside a predetermined range.

(11) The oxygen concentrator described in (10), wherein the control device is a control device performing a control without allowing the supply airflow volume of the compressed air supply device to decrease when the temperature sensor detects a value lower than a predetermined lower temperature limit of the threshold and the supply airflow volume is lower than a predetermined airflow volume during running of the oxygen concentrator.

(12) The oxygen concentrator described in (10) or (11), wherein the control device is a device performing a control that makes a supply airflow volume of the compressed air supply device to be higher than a supply airflow volume corresponding to an oxygen concentration value detected by the oxygen concentration sensor, regardless of the value detected by the oxygen concentration sensor when the temperature sensor detects a value lower than a predetermined lower temperature limit of the threshold on start-up of the oxygen concentrator.

(13) The oxygen concentrator described in any of (1) to (12), wherein the oxygen concentration sensor is a zirconia-type oxygen concentration sensor or an ultrasonic-type oxygen concentration sensor.

Effect of the Present Invention

According to the present invention, a highly concentrated oxygen can be provided constantly to a patient independently of environmental temperature by an oxygen concentrator performing control with which a supply airflow volume of a compressed air supply device is increased/decreased based on a value detected by an oxygen concentration sensor which detects an a oxygen gas concentration to maintain an oxygen concentration at a predetermined concentration, which concentrator has a temperature sensor which measures a gas temperature (environmental temperature), and depending on a detected temperature value, a decrease in supply volume of the compressed air supply device is not allowed, and airflow is supplied in a volume higher than a supply airflow volume corresponding to a detected oxygen concentration value on start-up so that an excessive decrease in supply air volume at low temperatures can be prevented.

Further, according to the present invention, reduction in oxygen concentration and unduly elevation in electric power consumption are prevented even when a tube is flattened or when the flow rate sensor and/or the flow rate adjustment device do not work normally by providing a flow rate sensor which measures an oxygen gas flow rate and performing control which does not allow increase/decrease in supply volume of the compressed air supply device depending on a detected flow rate value in the oxygen concentrator in which a supply airflow volume of the compressed air supply device is increased/decreased based on a value detected by the oxygen concentration sensor which detects oxygen gas concentration to maintain an oxygen concentration at a predetermined concentration.

BRIEF DESCRIPTION OF DRAWINGS

The application file contains at least one drawing executed in color. Copies of this patent or patent application publication with color drawing(s) will be provided by the Office upon request and payment of the necessary fee.

EXPLANATION OF NUMERALS

1. Oxygen concentrator
3. User (patient)
101. External air intake filter
103. Compressor
104. Switching valve
105. Adsorption cylinder
106. Equalizing valve
107. Check valve
108. Product tank
109. Pressure regulating valve
110. Flow rate setting device
111. Filter
301. Oxygen concentration sensor
302. Flow rate sensor
303. Temperature sensor
401. Control device
402. Recording device

BEST MODE FOR CARRYING OUT THE PRESENT INVENTION

An oxygen concentrator, an example of illustrative embodiment of the present invention, will be described with reference to the drawings below. The present invention is not restricted by these embodiments in any way.

Figure 1:
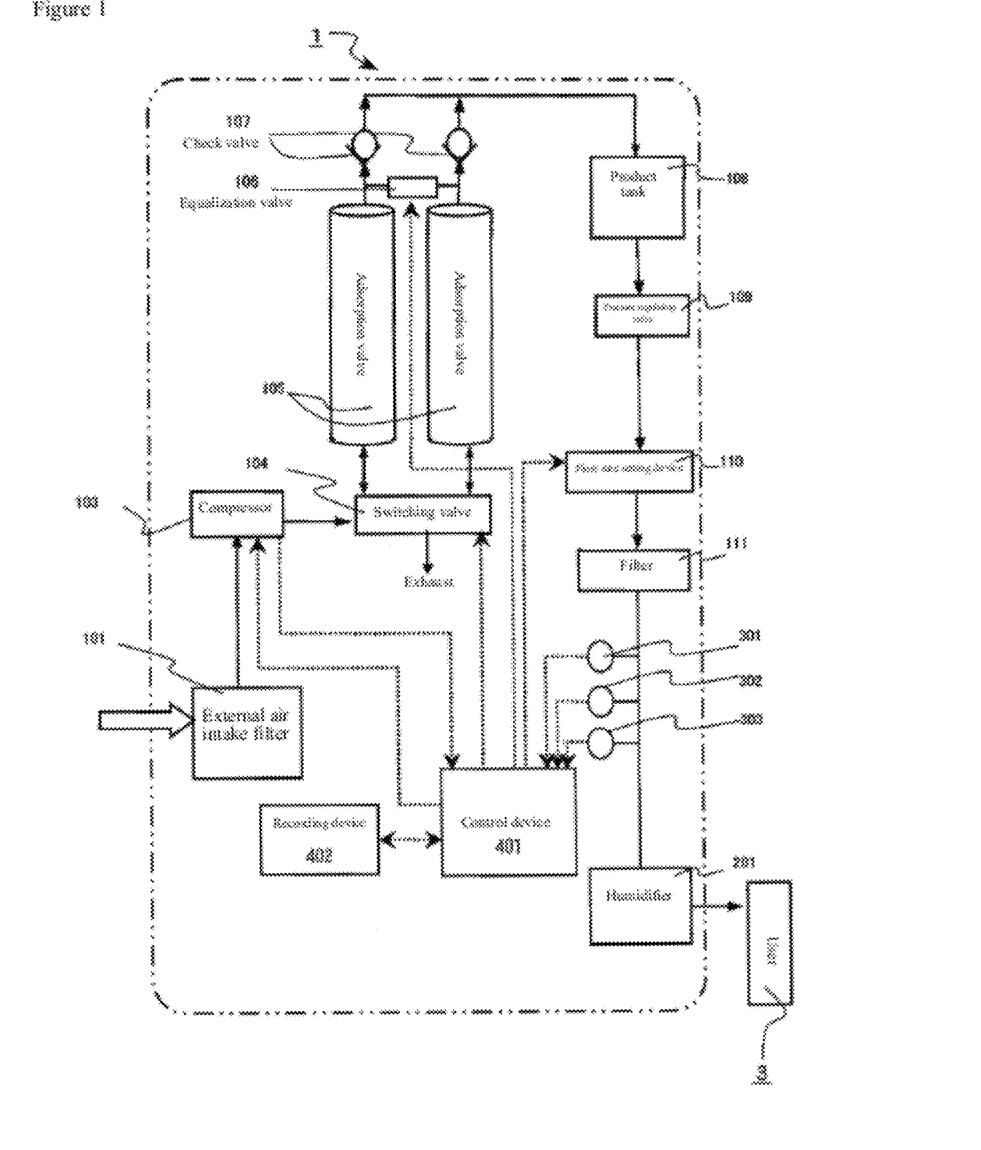
FIG. 1 is a schematic constitutional diagram of the oxygen concentrator according to the present invention.

FIG. 1 is a schematic constitutional diagram of an apparatus illustrating one embodiment of the pressure swing adsorption-type oxygen concentrator of the present invention. In FIGS. 1, 1 and 3 represent an oxygen concentrator and a user (patient) inhaling humidified oxygen-enriched air, respectively. Pressure swing adsorption-type oxygen concentrator 1 is equipped with external air intake filter 101, compressor 103 that is a compressed air supply device, switching valve 104, adsorption cylinder 105, equalizing valve 106, check valve 107, product tank 108, pressure regulating valve 109, flow rate setting device 110 and filter 111. With this, oxygen-enriched air can be generated by concentrating an oxygen gas from raw material air brought in from outside.

Raw material air brought in an oxygen concentrator from outside is first taken in from an air intake port equipped with external air intake filter 101 to eliminate foreign particles such as dust and the like. At this time, ordinary atmospheric air contains about 21% oxygen gas, about 77% nitrogen gas, 0.8% argon gas and 1.2% gases such as steam and the like. Such an oxygen concentrator selectively concentrates and isolates only the oxygen gas required for a breathing gas.

For isolating such oxygen gas, raw material air is pressurized by compressor 103 to supply the air to adsorption cylinder 105 filled with an adsorbent containing zeolites and the like, which selectively adsorb nitrogen gas molecules relative to oxygen gas molecules, by successively switching targeted adsorption cylinders 105 by switching valve 104, and about 77% nitrogen gas contained in raw material air inside adsorption cylinder 105 is selectively adsorbed and eliminated.

Adsorption cylinder 105 described above is composed of a cylindrical vessel filled with the adsorbent described above and is generally available as a one cylinder-type, a two cylinder-type or further a multiple cylinder-type with three or more cylinders. A multiple cylinder-type of adsorption cylinders 105 is preferably used in order to continuously and effectively produce oxygen-enriched air from raw material air. A rotating-type air compressor such as screw-type, rotary-type, scroll-type air compressors and the like may be used in some cases as compressor 103 described above in addition to a reciprocating-type air compressor. The power source of a motor to drive this compressor 103 may be alternate current or direct current.

Oxygen-enriched air containing an oxygen gas as a main component, which is not adsorbed in adsorption cylinder 105 described above, is flown into product tank 108 via check valve 107 which is installed to prevent the gas from flowing back into adsorption cylinder 105.

Nitrogen gas adsorbed on the adsorbent filled in adsorption cylinder 105 is now required to be desorbed from the adsorbent in order to reuse the adsorbent to adsorb nitrogen gas again from freshly introduced raw material air. For this purpose, switching valve 104 is used to switch from a pressurized condition achieved by compressor 103 to a depressurized condition (for example, atmospheric pressure state or negative pressure state) to desorb the nitrogen gas adsorbed to regenerate the adsorbent. In this desorption step, an oxygen-enriched air may be flown back as a purge gas from the product outlet side of the adsorption cylinder during the adsorption step via equalizing valve 106 in order to increase a desorption efficiency.

Oxygen-enriched air is produced from raw material air and stored in product tank 108. The oxygen-enriched air stored in product tank 108 contains, for example, an oxygen gas highly concentrated to a level of 95%. While pressure regulating valve 109, flow rate setting device 110 and the like subsequently control the supply flow rate and the pressure, the oxygen-enriched air is fed to humidifier 201, from which a humidified oxygen-enriched air is supplied to patient. For such a flow rate setting device 110, in addition to an orifice-type flow rate setting device, a flow rate control valve such as a control valve (CV) and the like may be used.

A set value of flow rate setting device 110 that sets a supply flow rate of oxygen-enriched air, a concentration value on oxygen concentration sensor 301, an actual oxygen flow rate value on flow rate sensor 302 are detected, and the detection results are stored in recording device 402 such as memory and the like to monitor operating condition, and an oxygen production amount is adjusted based on the detection results. Accordingly, the number of revolutions of an electric motor for compressor 103 is controlled by control device 401 to control a supply volume of raw material air and switching timing of absorption and desorption is controlled by controlling switching valve 104. A zirconia-type oxygen sensor and an ultrasonic-type oxygen sensor may be used as the oxygen concentration sensor. A heat wire-type mass flow meter and an ultrasonic-type flow rate sensor may be used as the flow rate sensor. An ultrasonic-type sensor is preferable in terms of reductions in size and the number of components, since it enables measurements of oxygen concentration and oxygen flow rate with one sensor.

According to the present invention, control is performed to increase/decrease a supply airflow volume of the compressed air supply device based on a value detected by the oxygen concentration sensor which detects oxygen gas concentration to maintain an oxygen concentration at a predetermined concentration and temperature sensor 303 measuring temperature of the apparatus is provided and a control device is changed depending on a value measured by the temperature sensor. In the present specification, a control device performing control depending on a value measured by the temperature sensor also refers to as a temperature dependent control device.

The control which does not allow the decrease in supply airflow volume of the compressed air supply device is performed when the temperature sensor detected value detects a value lower than a predetermined lower temperature limit (threshold) and the control which makes a supply airflow volume of the compressed air supply device to be higher than a supply airflow volume corresponding to the detected oxygen concentration value, regardless of a value detected by the oxygen concentration sensor is performed when the temperature sensor detects a value lower than a lower temperature limit on apparatus start-up to prevent a product oxygen concentration from being lower than the predetermined concentration.

In other words, when a value detected by the temperature sensor detected value is lower than a predetermined lower temperature limit, control which decreases a supply airflow volume of the compressed air supply device such as a compressor and the like is not performed. At this time, a control which does not allow the decrease in supply airflow volume of the compressed air supply device when a supply airflow volume is lower than a predetermined airflow volume is performed in addition to the detection of a lower temperature limit, the accuracy of the control increases and it is preferable. The case where a supply airflow volume is lower than a predetermined airflow volume is a case where a supply airflow volume is lower than the supply airflow volume to secure a predetermined oxygen concentration in environment at a temperature lower than the predetermined lower temperature limit. In other words, a predetermined airflow volume is shown by a dotted line in FIG. 2 and the lowest supply airflow volume to enable a predetermined oxygen concentration in the environment at a temperature lower than a predetermined lower temperature limit (5° C. in FIG. 2).

Figure 2:
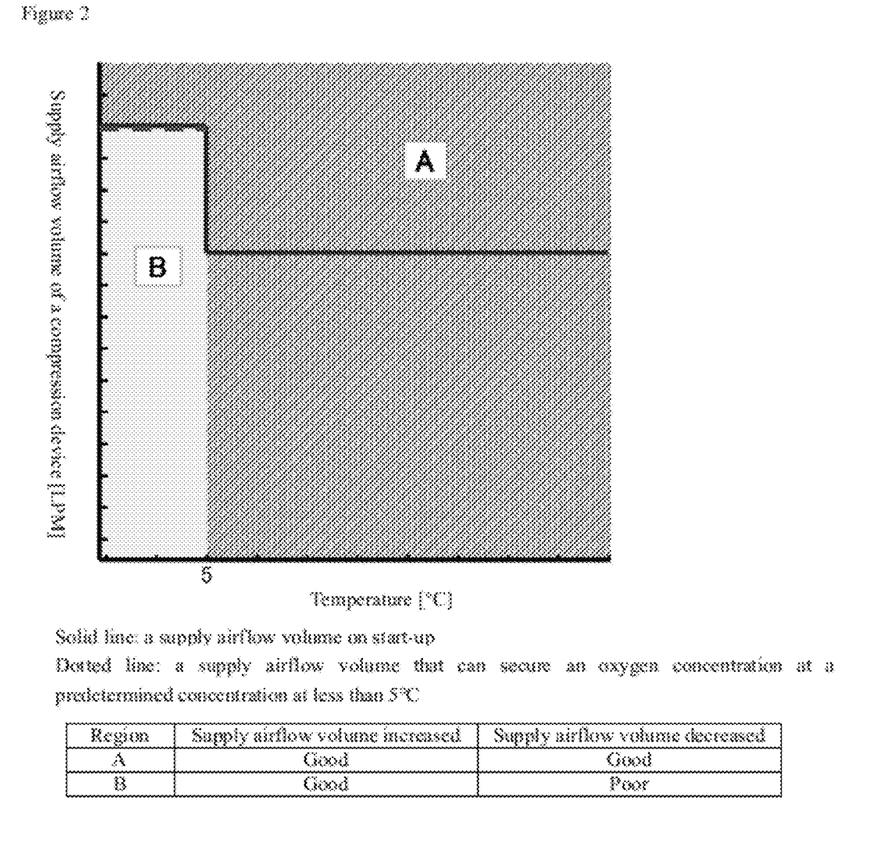
FIG. 2 is a schematic explanatory diagram of the control of the present invention.

Specifically, region B in FIG. 2 corresponds to the case where a value lower than the lower temperature limit is detected and a supply airflow volume is lower than a predetermined airflow volume. FIG. 2 explains the control depending on the temperature according to the present invention. In FIG. 2, a predetermined airflow volume is set to be the same as the supply airflow volume on start-up at a temperature lower than a lower temperature limit. A predetermined airflow volume is, for example, 1.05 to 1.2-fold increase of a supply airflow volume on start-up at a temperature of a lower temperature limit or higher, although it differs depending on a predetermined lower temperature limit and a predetermined oxygen concentration. When a temperature sensor detected value detects a temperature lower than a predetermined lower temperature limit and a supply airflow volume is higher than a predetermined airflow volume, control which decreases the supply airflow volume of the compressed air supply device such as a compressor and the like is performed.

Specifically, this corresponds to region A at a temperature lower than a lower temperature limit in FIG. 2. Region A is the shaded area in FIG. 2.

In addition, when a temperature sensor detects a temperature lower than a predetermined lower temperature limit on start-up of the apparatus, it is effective to increase a supply airflow volume in advance to promote softening of a piston ring, since the piston ring of a compressor in an oxygen concentrator using a compressor as the compressed air supply device is hardened. Accordingly, when the temperature sensor detects a temperature lower than a predetermined lower temperature limit on start-up of the apparatus, control which increases the supply airflow volume of the compressed air supply device such as a compressor and the like to supply at a higher volume than the supply airflow volume for a detected concentration value is performed. Although this higher supply airflow volume differs depending on the respective predetermined flow rate (formulated flow rate), it is, for example, 1.05 to 1.2-fold increase of a supply volume at a temperature of a lower temperature limit or higher and it can be set in advance.

As the control which increases/decreases a supply airflow volume of the compressed air supply device based on a value detected by the oxygen concentration sensor according to the present invention, a proportional (P) control in which an input value is manipulated in proportion to a deviation between a detected value and a target value of oxygen concentration, an integral (I) control in which an input value is manipulated in proportion to an integration value of deviations, a PI control combining these, and the like can be suitably used.

In addition, for the oxygen concentrator, it is desirable to set a stabilization time to the operation of the compressed air supply device, that is, the response time of oxygen concentration to be 5 to 10 minutes. According to the present invention, an increase/decrease in supply airflow volume of the compressed air supply device is determined based on a detected oxygen concentration value with an interval of 5 to 10-minute stabilization time.

Since an adsorption/desorption speed of the adsorbent decreases and a volume of nitrogen desorbed in the desorption step decreases at low temperatures, the volume of adsorbed nitrogen gradually increases. Accordingly, a response of a decrease in oxygen concentration by control of increasing/decreasing a supply airflow volume of the compressed air supply device, especially control of decreasing a supply airflow volume is delayed.

If a response time of oxygen concentration takes long, control may be overshot. Further, in an oxygen concentrator using an adsorbent, properties of the adsorbent differ depending on the temperatures and it is confirmed that a response time of oxygen concentration to supply airflow volume takes long when environmental temperature is low and the supply airflow volume is decreased.

The temperature at which a response time of oxygen concentration to supply airflow volume takes long to overshoot the control differs depending on the absorption processes and the amounts of the adsorbents. It has been confirmed that in the present invention, a remarkable decrease in oxygen concentration due to the overshoot of the above control is not observed, that is, response of the oxygen concentration to supply air volume is sufficient in environment at 5° C. Consequently, a lower temperature limit for a control at which a supply airflow volume of the compressed air supply device is decreased based on a detected oxygen concentration value may be 5° C. or higher. According to the present invention, the lower temperature limit for control to decrease a supply airflow volume of the compressed air supply device is 5° C.

When a temperature lower than 5° C. is detected during running and a supply airflow volume is lower than a predetermined airflow volume, control which decreases a supply airflow volume of the compressed air supply device based on a detected oxygen concentration value is stopped even when the oxygen concentration is higher than a predetermined value. On the other hand, control which increases a supply airflow volume of the compressed air supply device based on a detected oxygen concentration value is maintained when an oxygen concentration is lower than a predetermined value. When a value lower than 5° C. is maintained, this control is performed, and when a value detected by the temperature sensor exceeds 5° C., the control is switched to ordinary control of a supply airflow volume of the compressed air supply device based on a detected oxygen concentration value.

When the environmental temperature sensor detects a temperature lower than 5° C. on start-up of the oxygen concentrator, a supply airflow volume of the air supply device is controlled to secure a predetermined product concentration at the lower temperature limit for guaranteed operation of the present invention, that is, environmental temperature of 5° C., and as long as the temperature sensor detects a temperature lower than 5° C., control which supplies air in a volume larger than the supply air volume is performed to prevent a decrease in concentration due to the overshooting of the control above.

In addition, when the temperature sensor then detects a temperature of 5° C. or higher, since overshooting of the control is not concerned, control which allows the supply airflow volume of the air supply device to decrease until the supply airflow volume corresponds to the oxygen concentration is performed, thereby decreasing the electric power consumption of the apparatus.

Further, when the temperature sensor detects a temperature of 5° C. or higher on start-up and then a temperature lower than 5° C. and a supply airflow volume is lower than a predetermined airflow volume, control which does not allow the supply airflow volume from the airflow volume supplied when the temperature sensor detects the temperature lower than 5° C. to decrease is performed.

Figure 3:
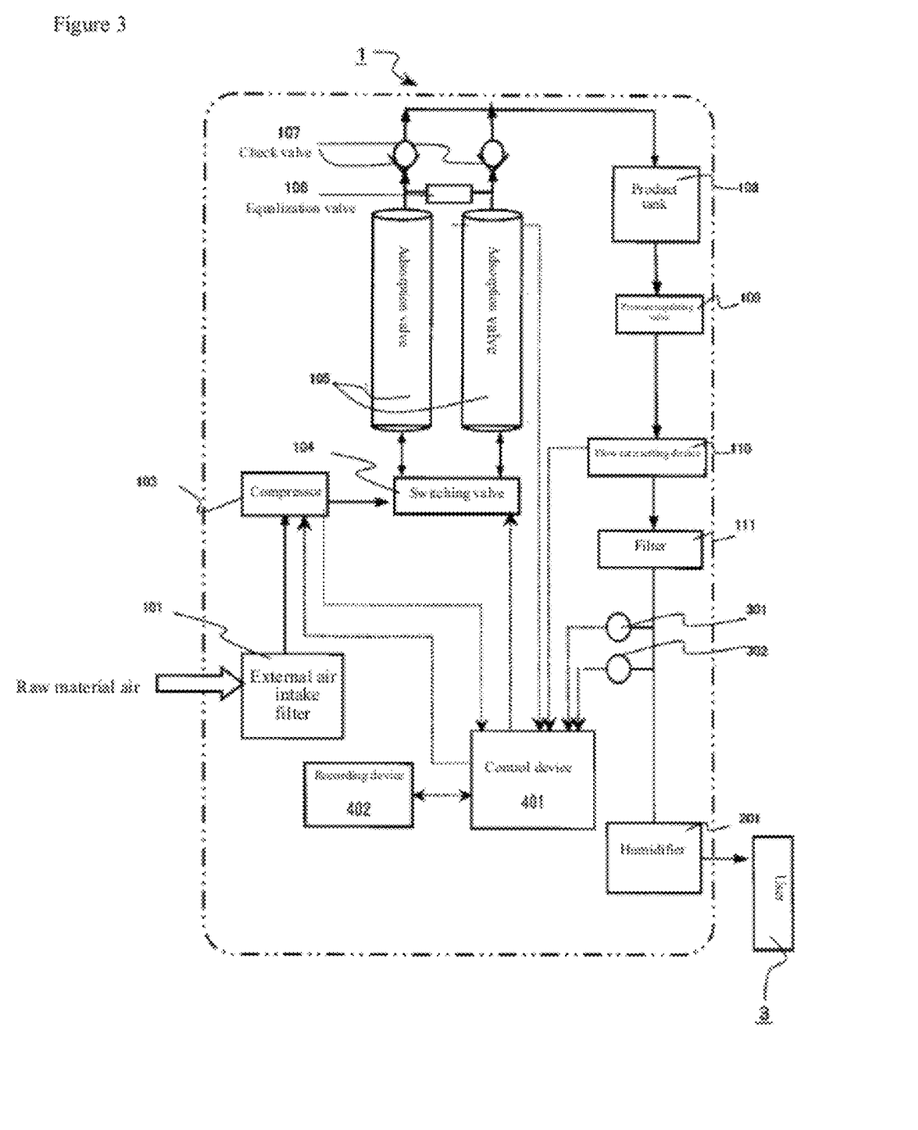
FIG. 3 is a schematic constitutional diagram of another aspect of the oxygen concentrator according to the present invention.

In another aspect of the present invention, an oxygen concentrator is provided, which performs control which increases/decreases the supply airflow volume of the compressed air supply device based on a value detected by an oxygen concentration sensor which detects oxygen gas concentration to maintain the oxygen concentration at a predetermined concentration and which is equipped with a flow rate sensor which measures oxygen gas supply flow rate and performs control which does not allow the supply airflow volume of the compressed air supply device to increase/decrease when a detected flow rate is outside the flow rate range determined in accordance with the set flow rate. Since the temperature sensor is not essential in this case, FIG. 3 shows an embodiment excluding a temperature sensor from FIG. 1. In the present specification, a control device performing control based on the detected flow rate value also refers to a flow rate dependent control device.

As the control which increases/decreases the supply airflow volume of the compressed air supply device based on the value detected by the oxygen concentration sensor, a proportional (P) control in which an input value is manipulated in proportion to a deviation between a detected value and a target value of oxygen concentration, an integral (I) control in which an input value is manipulated in proportion to integration value of deviations, a PI control combining the proportional (P) control and the integral (I) control, and the like may be suitably used.

According to the present invention, it is efficient to determine the control of the compressed air supply device at an interval of 5 to 10-minute stabilization time. Especially when an oxygen flow rate is decreased over a long time due to tube flattening and the like during sleeping and the like to increase an oxygen concentration, leading to a decrease in the supply capacity of the compressed air supply device, however, a decrease in supply capacity at 5 to 10-minute intervals may lead to an unduly decrease in supply capacity of the compressed air supply device. Accordingly, if the oxygen flow rate returns to normal, an oxygen concentration alarm may be activated even though the apparatus is essentially not in trouble by the time when the capacity of the compressed air supply device returns to that required for normal oxygen flow rate.

According to the present invention, by not only detecting an oxygen concentration but also determining whether or not the supply airflow volume of the compressed air supply device is increased/decreased based on the detected oxygen gas flow rate value at an interval of 5 to 10-minute stabilization time, activation of unnecessary oxygen concentration alarm during normal operation of the apparatus is thus eliminated even when an oxygen concentration is increased or decreased due to the decrease or increase in oxygen flow rate and unnecessary increase in electric power consumption for increasing the capacity of the compressed air supply device may be suppressed.

Further, when the flow rate sensor accuracy required for the oxygen concentrator is taken into consideration, a flow rate outside ±10% of a set flow rate is highly possible to be an abnormal as the oxygen flow rate. The present invention enables to achieve the desired oxygen concentration and oxygen flow rate quickly when the apparatus returns to the normal condition.

Further, according to another aspect of the present invention, an oxygen concentrator is provided, which performs control that increases/decreases a supply airflow volume of the compressed air supply device oxygen based on a value detected by an oxygen concentration sensor which detects a gas concentration to maintain an oxygen concentration at a predetermined concentration, is provided with a temperature sensor that measures a temperature of the apparatus and switches a control device depending on the value measured by the temperature sensor, and also is provided with a flow rate sensor that measures an oxygen gas supply flow rate and perform control that does not allow the supply volume of the compressed air supply device to increase/decrease depending on the detected flow rate value.

As the oxygen concentrator, the apparatus having an oxygen concentration sensor, a flow rate sensor, and a temperature sensor as shown in FIG. 1 is applicable.

In other words, when the temperature sensor detected value detects a value lower than a predetermined lower temperature limit, and preferably a supply airflow volume of the compressed air supply device is also lower than a predetermined supply airflow volume, or when an oxygen gas supply flow rate is outside the flow rate range determined based on the set flow rate, control that does not allow the supply airflow volume of the compressed air supply device to decrease is performed; when an oxygen gas supply flow rate is outside the flow rate range determined based on the set flow rate, control that does not allow the supply airflow volume of the compressed air supply device to increase is performed; and further when a temperature lower than a lower temperature limit is detected on start-up of the apparatus, control that makes a supply airflow volume to be higher than the supply airflow volume corresponding to the detected oxygen concentration value is performed.

Since this aspect combines the control by temperature and the control by flow rate, described above, double explanation will be omitted. For example, the following matters are similar to those in the above aspects: the lower temperature limit is set at 5° C.; the threshold of a value detected by the flow rate sensor is allocated individually in accordance with a set value of the flow rate setting device or independently of the set flow rate; when a value detected by the flow rate sensor is +10% or higher or −10% or lower of the set value for the flow rate setting device, control that does not allow the supply airflow volume of the compressed air supply device to change is performed regardless of the detected value of an oxygen concentration sensor.

According to the present invention, a desired oxygen concentration is stably provided.

The invention claimed is:

1. An pressure swing adsorption-type oxygen concentrator provided with an adsorption bed filled with an adsorbent, which selectively adsorbs nitrogen relative to oxygen, and a compressed air supply device, which supplies compressed air to the adsorption bed, to adsorb and eliminate nitrogen in raw material air to produce unadsorbed oxygen and to supply an oxygen gas at a predetermined flow rate by a flow rate setting device, comprising:
   an oxygen concentration sensor, which detects a concentration of an oxygen gas produced by the oxygen concentrator,
   a temperature sensor, which measures an environmental temperature,
   a control device, which performs control by increasing or decreasing a supply airflow volume of the compressed air supply device based on a detected oxygen concentration value to maintain an oxygen concentration at a predetermined concentration,
   wherein the control device controls a supply airflow volume of the compressed air supply device based on a value detected by the temperature sensor when the value detected by the temperature sensor being outside a predetermined threshold,
   wherein the control device is a control device, which performs control without allowing the supply airflow volume of the compressed air supply device to decrease when the temperature sensor detects a value lower than a predetermined lower temperature limit of the threshold during running of the oxygen concentrator.

2. The oxygen concentrator according to claim 1, wherein the oxygen concentration sensor is a zirconia-type oxygen concentration sensor or an ultrasonic-type oxygen concentration sensor.

3. An pressure swing adsorption-type oxygen concentrator provided with an adsorption bed filled with an adsorbent, which selectively adsorbs nitrogen relative to oxygen, and a compressed air supply device, which supplies compressed air to the adsorption bed, to adsorb and eliminate nitrogen in raw material air to produce unadsorbed oxygen and to supply an oxygen gas at a predetermined flow rate by a flow rate setting device, comprising:
   an oxygen concentration sensor, which detects a concentration of an oxygen gas produced by the oxygen concentrator,
   a temperature sensor, which measures an environmental temperature,
   a control device, which performs control by increasing or decreasing a supply airflow volume of the compressed air supply device based on a detected oxygen concentration value to maintain an oxygen concentration at a predetermined concentration,
   wherein the control device controls a supply airflow volume of the compressed air supply device based on a value detected by the temperature sensor when the value detected by the temperature sensor being outside a predetermined threshold,
   wherein the control device is a control device, which performs control without allowing the supply airflow volume of the compressed air supply device to decrease when the temperature sensor detects a value lower than a predetermined lower temperature limit of the threshold and the supply airflow volume is lower than a predetermined airflow volume during running of the oxygen concentrator.

4. The oxygen concentrator according to claim 1, wherein the temperature dependent control device is a device, which performs control to make a supply airflow volume of the compressed air supply device to be higher than a supply airflow volume corresponding to an oxygen concentration value detected by the oxygen concentration sensor, regardless of the value detected by the oxygen concentration sensor when the temperature sensor detects a value lower than a predetermined lower temperature limit of the threshold on start-up of the oxygen concentrator.

5. The oxygen concentrator according to claim 2, wherein the lower temperature limit is 5° C.

6. An oxygen concentrator provided with an adsorption bed filled with an adsorbent, which selectively adsorbs nitrogen relative to oxygen and a compressed air supply device, which supplies compressed air to the adsorption bed to adsorb and eliminate nitrogen in raw material air to produce unadsorbed oxygen and to supply an oxygen gas at a predetermined flow rate by a flow rate setting device, comprising:
   an oxygen concentration sensor, which detects a concentration of an oxygen gas produced,
   a flow rate sensor, which measures an oxygen gas flow rate,
   a control device, which performs control by increasing or decreasing a supply airflow volume of the compressed air supply device based on a detected oxygen concentration value to maintain an oxygen concentration at a predetermined concentration, and
   wherein the control device performs control without allowing the supply airflow volume of the compressed air supply device to change when the value detected by the flow rate sensor being outside the predetermined range.

7. The oxygen concentrator according to claim 6, wherein a threshold of a value detected by the flow rate sensor is allocated individually in accordance with a set value of the flow rate setting device or independently of a set flow rate value.

8. The oxygen concentrator according to claim 7, wherein the control device is a device, which performs control without allowing the supply airflow volume of the compressed air supply device to change regardless of a value detected by the oxygen concentration sensor when the value detected by the flow rate sensor is +10% or higher or −10% or less of a set value of the flow rate setting device.

9. The oxygen concentrator according to claim 6, wherein the flow rate sensor is an ultrasonic-type flow rate sensor or a heat wire-type flow rate sensor.

10. An oxygen concentrator provided with an adsorption bed filled with an adsorbent, which selectively adsorbs nitrogen relative to oxygen and a compressed air supply device, which supplies compressed air to the adsorption bed, to adsorb and eliminate nitrogen in raw material air to produce unadsorbed oxygen and to supply an oxygen gas at a predetermined flow rate by a flow rate setting device, comprising:

an oxygen concentration sensor, which detects a concentration of an oxygen gas produced by the oxygen concentrator, a temperature sensor, which measuring an environmental temperature, a flow rate sensor, which measures an oxygen gas flow rate, a control device, which performs control by increasing or decreasing a supply airflow volume of the compressed air supply device based on a detected oxygen concentration value to maintain an oxygen concentration at a predetermined concentration, wherein the control device performs control of a supply airflow volume of the compressed air supply device based on a value detected by the temperature sensor when the value detected by the temperature sensor being outside a predetermined threshold, and wherein the control device performs flow rate dependent control without allowing the supply airflow volume of the compressed air supply device to change when the value detected by the flow rate sensor being outside a predetermined range.

11. The oxygen concentrator according to claim 10, wherein the control device is a control device, which performs control without allowing the supply airflow volume of the compressed air supply device to decrease when the temperature sensor detecting a value lower than a predetermined lower temperature limit of the threshold and the supply airflow volume being lower than a predetermined airflow volume during running of the oxygen concentrator.

12. The oxygen concentrator according to claim 10, wherein the control device is a device, which performs control that makes a supply airflow volume of the compressed air supply device to be higher than a supply airflow volume corresponding to an oxygen concentration value detected by the oxygen concentration sensor, regardless of the value detected by the oxygen concentration sensor when the temperature sensor detects a value lower than a predetermined lower temperature limit of the threshold on start-up of the oxygen concentrator.

* * * * *